United States Patent
Bell et al.

(10) Patent No.: US 9,765,408 B2
(45) Date of Patent: *Sep. 19, 2017

(54) PROCESS FOR CONTROLLING FERMENTATION OF CO-CONTAINING SUBSTRATES

(71) Applicant: INEOS BIO SA, Rolle (CH)

(72) Inventors: Peter Simpson Bell, Dunblane (GB); Song Liu, Fayetteville, AR (US)

(*) Notice: Subject to any disclaimer, the term of this patent is extended or adjusted under 35 U.S.C. 154(b) by 0 days.

This patent is subject to a terminal disclaimer.

(21) Appl. No.: 14/806,851

(22) Filed: Jul. 23, 2015

(65) Prior Publication Data

US 2016/0047007 A1 Feb. 18, 2016

Related U.S. Application Data

(60) Provisional application No. 62/036,239, filed on Aug. 12, 2014.

(51) Int. Cl.
*C12Q 3/00* (2006.01)
*C12P 7/06* (2006.01)

(52) U.S. Cl.
CPC .............. *C12Q 3/00* (2013.01); *C12P 7/06* (2013.01); *C12P 7/065* (2013.01); *Y02E 50/17* (2013.01)

(58) Field of Classification Search
CPC ...................................................... C12Q 3/00
See application file for complete search history.

(56) References Cited

U.S. PATENT DOCUMENTS 8,735,115 B2 * 5/2014 Mihalcea ............ C12P 7/54 435/161
2013/0316422 A1 11/2013 Scott et al.
2014/0220649 A1 8/2014 Tobey et al.

FOREIGN PATENT DOCUMENTS

WO 2010064933 6/2010

OTHER PUBLICATIONS

Younesi et al. Biochemical Engineering Journal, 2005, 27:110-119.*
Cotter et al. Enzyme and Microbial Technology, 2009, 44:281-288.*
Jenke J of Chromatographic Science, 2011, 49:524-539.*
International Searching Authority, International Search Report and Written Opinion issued in PCT/US2015/041893, mailed on Oct. 26, 2015, 4 pages.
Ying Guo, et al., Medium Optimization for Ethanol Production with Clostridium Autoethanogenum with Carbon Monoxide as Sole Carbon Source, Elsevier, Bioresource Technology 101 (2010) 8784-8789, 6 pages.
Michael Kopke, et al., Fermentative Production of Ethanol from Carbon Monoxide, ScienceDirect, Elsevier, Current Opinion in Biotechnology 2011, 22:320-325, 6 pages.
Jie Gao, et al., Development of Low Cost Medium for Ethanol Production from Syngas by Clostridium Rasdalei, Elsevier, Bioresource Technology 147 (2013) 508-515, 8 pages.
Jyotisna Saxena, et al., Optimization of a Corn Steep Medium for Production of Ethanol from Synthesis Gas Fermentation by Clostridium Ragsdalei, World J. Microbial Biotechnol (2012) 28:1553-1561, 10 pages.
Jyotisna Saxena, et al., Effect of Trace Metals on Ethanol Production from Synthesis Gas by the Ethanologenic Acetogen, *Clostridium ragsdalei*, J Ind Microbiol Biotechnol (2011) 38:513-521, 10 pages.

* cited by examiner

*Primary Examiner* — Bin Shen
(74) *Attorney, Agent, or Firm* — James P. Krueger

(57) ABSTRACT

A process for stable fermentation of CO-containing substrates and improved ethanol productivity includes providing medium components in amounts needed by microorganisms in the fermentation. The process includes determining a potassium concentration in the fermentation medium and providing a first medium and a second medium to the fermentation, the first medium provided at a rate effective for maintaining the potassium in the fermentation medium in a range of about 20 to about 200 mg/L until reaching a target cell density.

12 Claims, No Drawings

PROCESS FOR CONTROLLING FERMENTATION OF CO-CONTAINING SUBSTRATES

This application claims the benefit of U.S. Provisional Application No. 62/036,239, filed Aug. 12, 2014, which is incorporated in its entirety herein by reference.

A process is provided for fermenting a CO-containing substrate. More specifically, the process includes determining a nutrient concentration in the fermentation medium and maintaining those concentrations within concentration ranges. The process further includes maintaining certain nutrient concentrations effective for providing an STY of 10 g total alcohol/(L·day) or more.

BACKGROUND

Fermentations take place in defined liquid mediums. These mediums will typically include various macro- and micro-nutrient sources that are important in improving fermentation performance. Mediums used in connection with less common substrates, such as gaseous substrates, require well defined mediums to optimize performance. Anaerobic fermentations also require well defined mediums.

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

U.S. Pat. No. 7,285,402 describes mediums known for use in anaerobic fermentation of gaseous substrates to produce ethanol. Various component and component concentrations in the medium are effective for providing high levels of ethanol productivity. Providing certain medium components at various times during fermentation as needed by the microorganisms may provide for improved ethanol productivity and more stable fermentation processes.

SUMMARY

A process for stable fermentation of CO-containing substrates and improved ethanol productivity includes providing medium components in amounts needed by microorganisms in the fermentation. More specifically, a process for fermenting a CO-containing substrate includes providing the CO-containing substrate to a fermentation and fermenting the CO-containing substrate. The process further includes monitoring nutrient concentrations in a fermentation medium using a technique selected from the group consisting of ion chromatography, inductively coupled plasma spectrometry, ion-selective electrodes, flame photometry, flame ionization atomic absorption and combinations thereof.

In another aspect, a process for fermenting a CO-containing substrate includes providing the CO-containing substrate to a fermentation and fermenting the CO-containing substrate; determining a potassium concentration in the fermentation medium; and providing a first medium and a second medium to the fermentation, the first medium provided at a rate effective for maintaining the potassium in the fermentation medium in a range of about 20 to about 200 mg/L until reaching a target cell density.

DETAILED DESCRIPTION

The following description is not to be taken in a limiting sense, but is made merely for the purpose of describing the general principles of exemplary embodiments. The scope of the invention should be determined with reference to the claims.

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

"Carbonaceous material" as used herein refers to carbon rich material such as coal, and petrochemicals. However, in this specification, carbonaceous material includes any carbon material whether in solid, liquid, gas, or plasma state. Among the numerous items that can be considered carbonaceous material, the present disclosure contemplates: carbonaceous material, carbonaceous liquid product, carbonaceous industrial liquid recycle, carbonaceous municipal solid waste (MSW or msw), carbonaceous urban waste, carbonaceous agricultural material, carbonaceous forestry material, carbonaceous wood waste, carbonaceous construction material, carbonaceous vegetative material, carbonaceous industrial waste, carbonaceous fermentation waste, carbonaceous petrochemical co-products, carbonaceous alcohol production co-products, carbonaceous coal, tires, plastics, waste plastic, coke oven tar, fibersoft, lignin, black liquor, polymers, waste polymers, polyethylene terephthalate (PETA), polystyrene (PS), sewage sludge, animal waste, crop residues, energy crops, forest processing residues, wood processing residues, livestock wastes, poultry wastes, food processing residues, fermentative process wastes, ethanol co-products, spent grain, spent microorganisms, or their combinations.

The term "fibersoft" or "Fibersoft" or "fibrosoft" or "fibrousoft" means a type of carbonaceous material that is produced as a result of softening and concentration of various substances; in an example carbonaceous material is produced via steam autoclaving of various substances. In another example, the fibersoft can include steam autoclaving of municipal, industrial, commercial, and medical waste resulting in a fibrous mushy material.

The term "municipal solid waste" or "MSW" or "msw" means waste that may include household, commercial, industrial and/or residual waste.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

"Ton" or "ton" refers to U.S. short ton, i.e. about 907.2 kg (2000 lbs).

As used herein, productivity is expressed as STY. In this aspect, alcohol productivity may be expressed as STY (space time yield expressed as g ethanol/(L·day).

CO-Containing Substrate

A CO-containing substrate may include any gas that includes CO. In this aspect, a CO-containing gas may include syngas, industrial gases, and mixtures thereof.

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate mainly includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The CO-containing substrate will have a $CO/CO_2$ ratio of at least about 0.75, in another aspect, at least about 1.0, and in another aspect, at least about 1.5.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bio-products from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* 0-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

The fermentation should desirably be carried out under appropriate conditions for the desired fermentation to occur (e.g. CO-to-ethanol). Reaction conditions that should be considered include pressure, temperature, gas flow rate, liquid flow rate, medium pH, medium redox potential, agitation rate (if using a stirred tank reactor), inoculum level, maximum gas substrate concentrations to ensure that CO in the liquid phase does not become limiting, and maximum product concentrations to avoid product inhibition.

The methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough.

Startup:

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

As used herein, target cell density means a cell density of about to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

Post-Startup:

Upon reaching desired levels, liquid phase and cellular material is withdrawn from the reactor and replenished with medium. The process is effective for increasing cell density to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

Determination of Nutrient Concentration

In one aspect, the process includes determining a nutrient concentration in the fermentation medium. Nutrients concentrations monitored may include K, Mg, P and mixtures thereof. In this aspect, nutrient concentration, particularly potassium concentration, may be determined using ion chromatography (IC), inductively coupled plasma spectrometry (ICP), ion-selective electrodes, flame photometry, flame ionization atomic absorption and combinations thereof. Some examples of methods which may be utilized include: Small, Hamish (1989). *Ion chromatography*. New York: Plenum Press. ISBN 0-306-43290-0; Tatjana Weiss; Weiss, Joachim (2005). *Handbook of Ion Chromatography*. Weinheim: Wiley-VCH. ISBN 3-527-28701-9; Gjerde, Douglas T.; Fritz, James S. (2000). *Ion Chromatography*. Weinheim: Wiley-VCH. ISBN 3-527-29914-9; Joachim Weiss, Tatjana Weiss (Translated by) (2005). Handbook of Ion Chromatography, Third, Completely Revised and Enlarged Edition. John Wiley and Sons, Inc. 931p. ISBN: 3-527-28701-9; and Jackson, Peter; Haddad, Paul R. (1990). *Ion chromatography: principles and applications*. Amsterdam: Elsevier. ISBN 0-444-88232-4; all of which are incorporated herein by reference. Some examples of equipment which may be used include IC available from Thermo Scientific Dionex (www.thermoscientific.com/dionex) and OFITE (Houston, Tex.—www.ofite.com).

In another aspect, the process may further include determining concentrations of potassium, magnesium and/or $PO_4^{-3}$ in the fermentation medium. In this aspect, the process may include monitoring and controlling any one of or any combination of potassium, magnesium and $PO_4^{-3}$. The following table provides one example of elements and compositions utilized.

| Element | Added As |
|---|---|
| $Zn^{+2}$ | $ZnSO_4 \cdot 7H_2O$ |
| $Co^{+2}$ | $CoCl_2 \cdot 6H_2O$ |
| $Ni^{+2}$ | $NiCl_2 \cdot 6H_2O$ |
| $Fe^{+2}$ | $FeCl_2 \cdot 4H_2O$ |
| $K^+$ | KCl |
| $Mg^{+2}$ | $MgCl_2 \cdot 6H_2O$ |
| $P^{+5}/PO_4^{-3}$ | $H_3PO_4(85\%)$ |

Medium Compositions and Control of Medium Feed Rates

Effective medium compositions are described in U.S. Ser. Nos. 13/889,700, filed May 8, 2013, and U.S. Ser. Nos. 13/890,324 and 13/890,777, both filed May 9, 2013, all of which are incorporated herein by reference.

The fermentation medium includes less than about 0.01 g/L yeast extract and less than about 0.01 g/L carbohydrates.

Sulfur is supplied to the fermentation in the form of NaHS. In this aspect, a concentration of about 20 to about 500 ppm $H_2S$ is maintained in the fermentation off-gas by adding an effective amount of NaHS to the fermentation medium. In another aspect, about 200 to about 500 ppm $H_2S$ is maintained in the fermentation off-gas, in another aspect, about 250 to about 450 ppm $H_2S$ is maintained in the fermentation off-gas, and in another aspect, about 300 to about 400 ppm $H_2S$ is maintained in the fermentation off-gas.

Process operation maintains a pH in a range of about 3.5 to about 5.0, and in another aspect, about 4 to about 5. Nitrogen source (N) is provided through ammonium hydroxide, which is added as separate feed stream under pH control—as a result, $NH_4+$ will be in slight excess in the range of hundreds ppm.

In accordance with one aspect of the process, a first and second medium are provided to the fermentation. In this aspect, the first medium is provided at a rate effective for maintaining the potassium in the fermentation medium in a range of about 20 to about 200 mg/L until reaching a target cell density. In another aspect, the potassium in the fermentation medium is maintained in a range of about 20 to about 160 mg/L, in another aspect, about 20 to about 100 mg/L, in another aspect, about 110 to about 190 mg/L, in another aspect, about 120 to about 180 mg/L, in another aspect, about 130 to about 170 mg/L, and in another aspect, about 140 to about 160 mg/L. Upon reaching a target cell density, the first and second medium are provided at a rate effective for maintaining the potassium concentration in the fermentation medium in a range of about 20 to about 160 mg/L, in another aspect, about 20 to about 50 mg/L, and in another aspect, about 30 to about 40 mg/L.

In another aspect, medium is provided at a rate effective for maintaining the $PO_4^{-3}$ concentration in a range of about 10 to about 120 mg/L, in another aspect, about 10 to about 100 mg/L, in another aspect, about 10 to about 80 mg/L, in another aspect, about 10 to about 50 mg/L, and in another aspect, about 10 to about 25 mg/L. Upon reaching a target cell density, the first and second medium are provided at a rate effective for maintaining the $PO_4^{-3}$ concentration in the fermentation medium in a range of about 10 to about 120 mg/L, in another aspect, about 10 to about 80 mg/L, in another aspect, about 10 to about 40 mg/L, and in another aspect, about 10 to about 25 mg/L.

In another aspect, medium is provided at a rate effective for maintaining the Mg concentration in a range of about 1 to about 6 mg/L, in another aspect, about 1 to about 4 mg/L, and in another aspect, about 1 to about 3 mg/L, until reaching a target cell density. Upon reaching a target cell density, the first and second medium are provided at a rate effective for maintaining the magnesium concentration in the fermentation medium in a range of about 1 to about 6 mg/L, in another aspect, about 1 to about 4 mg/L, and in another aspect, about 1 to about 3 mg/L.

In another aspect, medium is provided to the fermentation at a rate effective for maintaining a volumetric flow rate ratio of the first medium to the second medium of about 15:1 to about 2:1, in another aspect, about 10:1 to about 2:1, and in another aspect, about 4:1 to about 2:1.

In another aspect, the process includes nutrient feed rate control to achieve desired nutrient concentrations. In this aspect, if potassium levels are found to be greater than about 50 mg/L, then the amount of the first medium is reduced about 10% every 4 hours until reaching a target potassium level. In another aspect, if phosphate levels are found to be less than about 10 ppm, then the amount of the first medium is increased about 10% every hour until reaching a target phosphate level. In another aspect, if magnesium levels are found to be less than about 1 mg/L, then the amount of the first medium is increased about 10% every hour until reaching a target magnesium level.

Syngas fermentations conducted in bioreactors with medium and acetogenic bacteria as described herein are effective for providing conversions of CO in syngas into alcohols and other products. In this aspect, alcohol productivity may be expressed as STY (space time yield expressed as g ethanol/(L·day). In this aspect, the process is effective for providing a STY (space time yield) of at least about 10 g ethanol/(L·day). Possible STY values include about 10 g ethanol/(L·day) to about 200 g ethanol/(L·day), in another aspect, about 10 g ethanol/(L·day) to about 160 g ethanol/(L·day), in another aspect, about 10 g ethanol/(L·day) to about 120 g ethanol/(L·day), in another aspect, about 10 g ethanol/(L·day) to about 80 g ethanol/(L·day), in another aspect, about 10 g ethanol/(L·day) to about 15 g ethanol/(L·day), in another aspect, about 15 g ethanol/(L·day) to about 20 g ethanol/(L·day), in another aspect, about 20 g ethanol/(L·day) to about 140 g ethanol/(L·day), in another aspect, about 20 g ethanol/(L·day) to about 100 g ethanol/(L·day), in another aspect, about 40 g ethanol/(L·day) to about 140 g ethanol/(L·day), in another aspect, about 40 g ethanol/(L·day) to about 100 g ethanol/(L·day), in another aspect, about 10 g ethanol/(L·day), in another aspect, about 15 g ethanol/(L·day), and in another aspect, about 16 g ethanol/(L·day).

While the invention herein disclosed has been described by means of specific embodiments, examples and applications thereof, numerous modifications and variations could be made thereto by those skilled in the art without departing from the scope of the invention set forth in the claims.

What is claimed is:

1. A process for controlling fermentation of a CO-containing substrate, the process comprising:
   providing the CO-containing substrate to a fermentation and fermenting the CO-containing substrate with acetogenic bacteria; and
   monitoring nutrient concentration in a fermentation medium using a technique selected from the group consisting of ion chromatography, inductively coupled plasma spectrometry, ion-selective electrodes, flame photometry, flame ionization atomic absorption and combinations thereof,
   wherein the nutrient being monitored are K, $PO_4^{-3}$, Mg and mixtures thereof,
   wherein the fermentation medium includes a first and a second nutrient containing medium and the monitoring step comprising providing the first medium to the fermentation at a rate effective for maintaining a potassium concentration in the medium of about 20 to about 200 mg/L until reaching a target cell density of about 2 to about 30 g/L and providing the first medium to the fermentation at a rate effective for maintaining a potassium concentration in the medium of about 20 to about 160 mg/L after reaching the target cell density.

2. The process of claim 1 wherein the technique used to monitor nutrient concentration is ion chromatography.

3. The process of claim 1 wherein the second medium is provided to the fermentation at a rate effective for maintaining a volumetric flow rate ratio of the first medium to the second medium of about 15:1 to about 2:1.

4. The process of claim 1 wherein the first medium includes elements selected from the group consisting of K, Mg, Fe, $PO_4^{-3}$, Zn, Co, Ni and mixtures thereof.

5. The process of claim 1 wherein the second medium includes elements selected from the group consisting of W, Se and mixtures thereof.

6. The process of claim 1 wherein the CO-containing substrate has a $CO/CO_2$ molar ratio of at least about 0.75.

7. The process of claim 1 wherein the CO-containing substrate has about 20 to about 100 mole % CO.

8. The process of claim 1 wherein a pH of the fermentation medium is maintained at level of about 3.5 to about 5.0.

9. The process of claim 8 wherein the pH is maintained with addition of ammonium hydroxide.

10. The process of claim 1 further comprising maintaining a concentration of $H_2S$ in fermentation off-gas in a range of about 20 to about 500 ppm $H_2S$.

11. The process of claim 10 wherein a concentration of about 20 to about 500 ppm $H_2S$ in the fermentation off-gas is maintained by adding NaHS to the fermentation medium.

12. The process of claim 1 wherein the acetogenic bacteria is selected from the group consisting of *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

* * * * *